(12) United States Patent
Pinnow

(10) Patent No.: US 10,045,821 B2
(45) Date of Patent: Aug. 14, 2018

(54) APPARATUS AND METHODS FOR SIDE-FIRE OPTICAL FIBER DEVICE SUITABLE FOR MEDICAL APPLICATONS

(71) Applicant: Douglas Arthur Pinnow, Lake Elsinore, CA (US)

(72) Inventor: Douglas Arthur Pinnow, Lake Elsinore, CA (US)

(73) Assignee: Douglas A. Pinnow, Lake Elsinore, CA (US)

( * ) Notice: Subject to any disclaimer, the term of this patent is extended or adjusted under 35 U.S.C. 154(b) by 0 days.

(21) Appl. No.: 15/338,420

(22) Filed: Oct. 30, 2016

(65) Prior Publication Data

US 2017/0128133 A1    May 11, 2017

Related U.S. Application Data

(60) Provisional application No. 62/252,471, filed on Nov. 7, 2015.

(51) Int. Cl.
| | |
|---|---|
| G02B 6/26 | (2006.01) |
| A61B 18/22 | (2006.01) |
| G02B 6/44 | (2006.01) |
| A61B 18/20 | (2006.01) |
| A61B 18/00 | (2006.01) |

(52) U.S. Cl.
CPC ............ *A61B 18/22* (2013.01); *A61B 18/201* (2013.01); *G02B 6/262* (2013.01); *G02B 6/4483* (2013.01); *G02B 6/4486* (2013.01); *A61B 2018/00029* (2013.01); *A61B 2018/206* (2013.01); *A61B 2018/2205* (2013.01); *A61B 2018/2272* (2013.01); *A61B 2018/2277* (2013.01)

(58) Field of Classification Search
None
See application file for complete search history.

(56) References Cited

U.S. PATENT DOCUMENTS

| | | | | |
|---|---|---|---|---|
| 5,253,312 A | * | 10/1993 | Payne | A61B 18/22 385/123 |
| 5,257,991 A | * | 11/1993 | Fletcher | A61B 5/0084 606/15 |
| 5,354,294 A | * | 10/1994 | Chou | A61B 18/24 606/11 |
| 5,486,171 A | * | 1/1996 | Chou | A61B 18/24 606/11 |
| 5,562,657 A | * | 10/1996 | Griffin | A61B 18/245 606/13 |

(Continued)

*Primary Examiner* — Sung Pak
(74) *Attorney, Agent, or Firm* — Douglas A. Pinnow

(57) ABSTRACT

This invention relates to an advance in the delivery of laser beams to internal surgical sites using optical fibers with a novel distal tip design made using a fusion assembly procedure suitable for directing laser beams out of the side of an optical fiber. This side-fire fiber delivery tip assembly is fabricated by fusing a transparent tube onto the distal ends of a laser beam delivery fiber and an associated coaxial stub fiber that have beveled and parallel end faces that meet inside of the transparent tube. The result is a rugged fiber delivery tip assembly that is almost entirely solid, except for a very narrow gap between the beveled end surfaces of the two fibers. A loose fitting transparent capsule may be placed over this fiber tip to contain a refractive index matching fluid that may also serve as a cooling agent for the fiber tip assembly.

19 Claims, 5 Drawing Sheets

(56) References Cited

U.S. PATENT DOCUMENTS

| | | | | |
|---|---|---|---|---|
| 8,724,941 B2* | 5/2014 | Reever | ............... | A61B 18/24 385/31 |
| 2006/0282068 A1* | 12/2006 | Griffin | ............... | A61B 18/22 606/13 |
| 2011/0082450 A1* | 4/2011 | Melsky | ............... | A61B 18/24 606/14 |

* cited by examiner

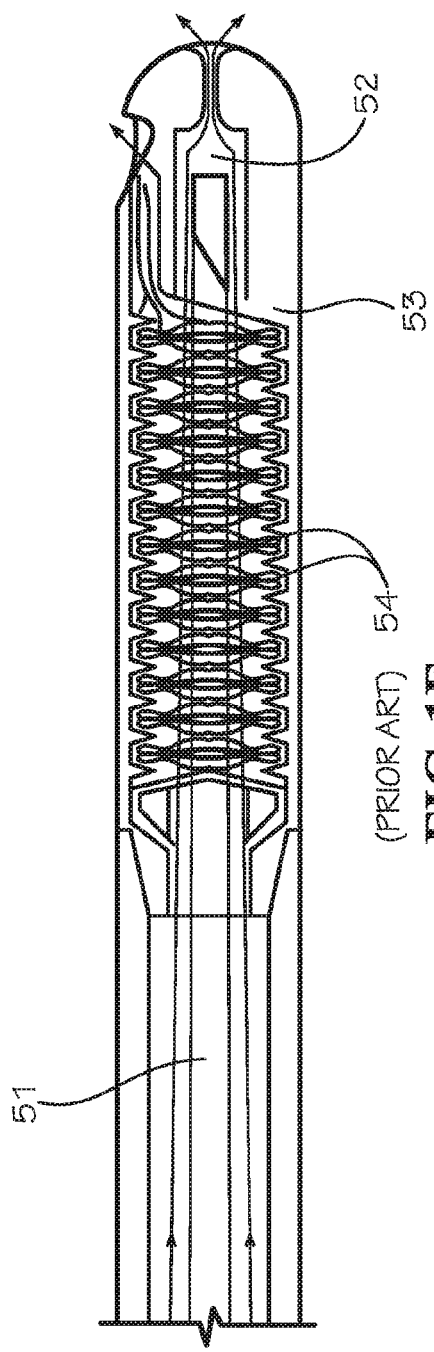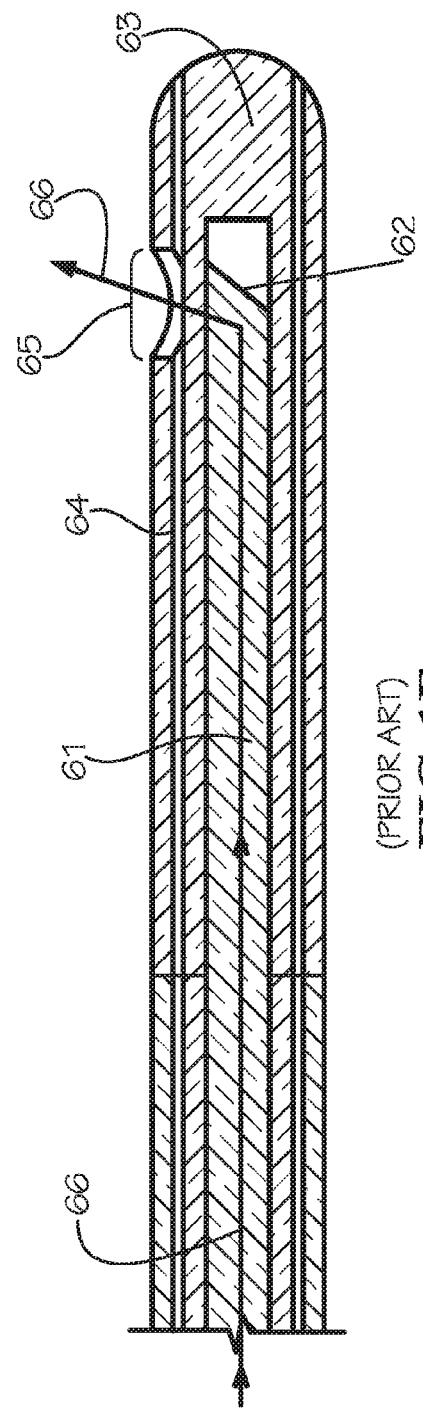
(PRIOR ART)
FIG. 1E
(PRIOR ART)
FIG. 1F

APPARATUS AND METHODS FOR SIDE-FIRE OPTICAL FIBER DEVICE SUITABLE FOR MEDICAL APPLICATONS

CROSS REFERENCES TO RELATED APPLICATIONS

This application claims the benefit of U.S. Provisional Patent Application Ser. No. 62/252,477 filed Nov. 7, 2015, titled IMPROVED APPARATUS AND METHODS FOR SIDE-FIRE OPTICAL FIBER DEVICE SUITABLE FOR MEDICAL APPLICATIONS and U.S. Provisional Patent Application Ser. No. 62/252,471 filed Nov. 7, 2015, titled LASER SURGERY EMPLOYING HEAVY WATER TO ENHANCE LASER BEAM TRANSMISSION the contents of which are hereby incorporated by reference herein.

TECHNICAL FIELD AND INDUSTRIAL APPLICABILITY OF THE INVENTION

Background of the Invention

1. Field of the Invention

This invention relates to enhancement of the delivery of laser beams to internal surgical sites, such as enlarged prostate glands (caused by benign prostate hyperplasia, BPH) or kidney stones, using optical fibers having a novel distal tip design for directing the laser beams out of the side surface of the optical fibers.

2. Description of Related Art

Over the past several decades, the medical uses of optical fibers to deliver both high and low power laser beams has substantially grown from primarily clinical trials to big business. One of the main driving forces for this trend has been the ability to insert small optical fibers into surgical cystoscopes and endoscopes to accomplish a broad range of surgical functions within the human body such as cutting, cauterizing, and ablating of tissues and fracturing hard objects, such as kidney stones.

At present, medical optical fiber device designs and techniques have reached a high level of development for firing a laser beam directly down the axis of a fiber and straight out of its end to accomplish a surgical function. This geometry is referred to in this paper as "end-fire". However, there is a class of surgical functions that can best be accomplished by having the laser beam exit the side of a fiber rather than its end. This geometry will be referred to as "side-fire". The side-fire technology is more complex than for end-fire and advancing this technology is still an active field of endeavor and the subject of this invention disclosure.

A good example of an application where side-fire capability is beneficial is in the treatment of BPH (benign prostatic hypertrophy). It is relatively easy to pass an optical fiber through the ureter and position it inside of a male patient's prostate gland. However, there is insufficient space to make a 90-degree bend of the fiber to redirect the distal tip of an end-fire fiber so that it is possible to ablate tissue in the surrounding prostate gland without breaking the fiber. However, a side-fire fiber is ideal for such a purpose because tissue ablation can be accomplished without bending the fiber. The fiber remains straight, but the laser beam comes out of the side of the fiber at close to a right angle from the axis of the fiber.

In the following discussion, one should keep in mind that the most demanding applications for side-fire optical fibers is to deliver laser beams with high optical power levels in the approximate range of, say, 20 to 200 Watts through the limited sized channels of modern cystoscopes/endoscopes that are typically 2 to 3 mm in diameter. This implies that the optical power density in the vicinity of the distal tip of the fiber will be so great that it is not only capable of performing the desirable effects of cutting, cauterizing, and ablating human tissue, but can also be self-destructive to the fiber or fiber delivery device if these components are not well designed and not operated while in competent surgical hands.

In fact, degradation to the point of inoperability is the norm for state-of-the-art high power side-fire fiber delivery devices used in present surgical applications. The design objective currently desired is not to eliminate the possibility of such degradation but to extend the useful working lifetime of the fiber delivery device sufficiently long to accomplish a specific surgical procedure before replacement is required. For example, a BPH treatment typically takes approximately 15 to 45 minutes to complete. So, 45 minutes is a practical minimum lifetime objective for a surgical side-fire optical fiber device in service. A related design objective for a side-fire fiber device is to detect and alert the surgeon of incipient failure of the device before catastrophic failure occurs that could cause broken glass pieces from the fiber to be disbursed in the surgical zone and that must be painstakingly retrieved.

Based on the above discussion, it is apparent that side-fire medical fibers used at present fall clearly into the category of medical disposables that are typically used either for a single procedure or, at most, a limited number of procedures. In fact, not infrequently, use of more than one side-fire fiber is required during a single procedure to avoid catastrophic failure.

While the technology that has been developed for side-fire optical fiber devices used in medical applications is extensive, the following discussion of the evolution of existing side-fire fiber tip designs establishes that while there have been significant advances in this field there is still considerable room for improvement. This discussion begins with an older unpublished U.S. patent application Ser. No. 08/111,884 filed Aug. 26, 1993 titled METHOD AND APPARATUS FOR ACTIVE CONTROL OF LASER ENERGY DENSITY DISTRIBUTION WITHIN A FIBER OPTIC DELIVERY DEVICE that is referred to herein as Brown '884. This patent application introduced fresh new ideas for making practical side-fire optical fiber devices. While this patent application has broader applicability than just for side-fire fibers, the discussion that follows is limited to the side-fire geometry.

Brown '884 recognized that it is imperative to keep the side-fire fiber tip clean and cool in order to avoid thermal destruction of the fiber. The concept for accomplishing this was to insert the fiber tip with a highly reflective optical coating applied on a beveled end surface into a transparent and loosely fitting capillary tube filled with transparent cooling fluid, either liquid or gas. (See Prior Art FIG. 1A, below.) The capillary tube may be either closed or partially open at the distal end. If the bevel angle were made 45 degrees to the fiber axis, the laser beam propagating down the axis of the optical fiber would be reflected off of the beveled mirror surface by an angle twice as large, 90 degrees, and continue out through the side-surface of the optical fiber.

Brown '884 has very little to say about the type of cooling fluid that should be used inside the capillary tube. However, this patent application recognized the desirability that the cooling "fluid varies in optical index between the light guiding means [optical fiber] and the capillary means

[tube]". This is in recognition of the fact that undesired reflections of the laser beam can be minimized at the interfaces between the optical fiber's surface and the cooling fluid and between the cooling fluid and the inner wall of the capillary tube by choosing a suitable fluid. For example, if air, with an index of refraction of approximately 1.0 were used as the cooling fluid, optical reflections of approximately 4% per interface would result in a total of 8% reflection loss for the two interfaces associated with the outer surface of the optical fiber and the inner surface of the capillary tube. On the other hand, if a liquid, such as water with an index of refraction of approximately 1.33, were used as the cooling fluid, these undesired reflections could be reduced to approximately 0.2% per interface. And, of course, if the index matching of the cooling liquid and the fused silica in the fiber and capillary tubes were perfect (having an index of refraction of, say, 1.46), the reflections would be entirely eliminated.

Since reflected light diminishes the power of the laser beam delivered to the surgical zone, the simple analysis above leads to preferential use of water or some other transparent liquid as the cooling fluid rather than a gas that would have a substantially lower refractive index than the optical fiber or glass in a surrounding capillary tube. However, this seemingly obvious choice of using a liquid with a reasonably good refractive index match to the optical fiber material has dire consequences if the mirror coating on the beveled tip of the optical fiber were to fail. In that case, the laser beam would no longer be reflected into the side-fire direction. Rather, the laser beam would continue forward in the general direction of the fiber's axis and could cause damage and undesired necrosis to perfectly good human tissue located in that direction.

Unfortunately, in the years since Brown '884 was filed in 1993, no one has succeeded in developing a reflective coating for an optical fiber that could endure a high power laser beam required for surgical applications for a sufficient period to complete a procedure, such as tissue ablation during BPH surgery. This represents a serious problem for the direct use of the Brown '884 design for side-fired fibers.

Fortunately, this problem does have a solution that has been adopted in all current high powered side-fired fiber delivery designs, as discussed next. The solution was first introduced several months after Brown '884 had been filed by Pon in patent number U.S. Pat. No. 5,428,699 titled PROBE HAVING OPTICAL FIBER FOR LATERALLY DIRECTING LASER BEAM referred to herein as Pon '699. The terminology "LATERALLY DIRECTING LASER BEAM" used in this title is synonymous to "side-fire". The present inventor has chosen to use the word "side-fire" since it describes the actual geometry and may leave a reader with a better intuitive impression.

The Pon '699 solution to the unavailability of a durable reflective coating for the beveled tips of side-fire fibers is deceptively simple, just eliminate the reflective coating, yet continue to get high efficiency reflections from the beveled tip of the fiber by a process known as total internal reflection. This is the same well known physical process that is used to guide light in all optical fibers.

In fact, the solution is not so simple for two reasons. First, the space directly adjacent to the beveled surface of the fiber tip must contain either a gas or a vacuum (having a refractive index of close to or equal to one). Use of a cooling liquid in that region is no longer possible because its higher refractive index would "frustrate" (i.e. inhibit) the total internal reflection process. The second reason is that there are angular limitations for the total internal reflection process which limit the reflected angle to approximately 79 degrees rather than the preferred 90 degrees. (See prior art FIG. 1B, below.) Even so, the 79 degree side-fire angle has proven to be generally acceptable for laser surgery.

A simple way to achieve such a gas or vacuum filled space adjacent to the beveled end surface of the optical fiber is described in Pon '699. A transparent capsule may be slid over the fiber tip and secured in place with an optically transparent bonding agent that would resist ingress of cooling and irrigation fluid and therefore leave an empty hollow space above the beveled fiber surface (see Prior Art FIG. 1B, below). However, it was quickly learned that existing optical bonding agents exhibited marginal ability to survive under direct illumination of a high power surgical laser beam. One way used to resolve this problem was to relocate the cement bond between the fiber and the transparent cap away from direct illumination of the side-fired laser beam by moving it further down the fiber from its tip as described in U.S. Pat. No. 7,909,817 B2 issued on Mar. 22, 2011 titled LATERAL LASER FIBER FOR HIGH AVERAGE POWER AND PEAK PULSE ENERGY and referred to herein as Griffin '817.

It is clear from reading Griffin '817 that moving the cement bond away from direct illumination by the laser beam is only a partial solution. That is because about 4 percent of the laser beam passing out of the side surface of the fiber is reflected backwards and another 4 percent is again reflected backwards upon entry into the transparent capsule. And these reflections are highly undesirable since they inevitably result in substantial heating of the fiber tip region. Their origin is well known as Fresnel reflections that are due to a refractive index mismatch between the fused silica (use in the optical fiber and, frequently, in the capsule) and the air or vacuum within the small space between the fiber side-surface and inner capsule surface. The dilemma is that the only way to eliminate these reflections would be to fill the space between the fiber side-surface and the capsule with a refractive index matching material that would, unfortunately, also fill the hollow region above the beveled surface and frustrate the necessary total internal reflection of the surgical laser beam.

Griffin '817 mentions the possibility of fusing (welding) the capsule directly to the fiber tip to eliminate the Fresnel reflections and describes two such designs in U.S. Pat. No. 5,562,657 (Griffin '657) and U.S. Pat. No. 5,537,499 (Brekke '499). See, for example, Prior Art FIG. 1C. below. Griffin '817 goes on to say "Both are high efficiency designs that utilize fiber-to-cap fusion to minimize scatter. Both fail at approximately 40 W [Watts] through catastrophic disintegration. It is thought that the residual stress concentration in the fiber-to-cap fusion region likely render the fused fibers more susceptible to the thermal shocks encountered in the surgery than non-fused fibers".

Griffin '817 also discuss several ways besides fusing to mitigate the effects of the undesired Fresnel reflections such as applying a reflective coating on the outer rear surface of the capsule to redirect a portion of the reflected light back towards the main laser beam (see prior art FIG. 1D, below) as well as using complicated cooling channels within the capsule to remove the excess heat generated as a consequence of the Fresnel reflections (see Prior Art FIG. 1E, below). However, neither method has proved to be without problems. For example, Griffin '817 states "At high average [laser] power or peak pulse energy, a gold [reflective coating on the reverse outer surface of the capsule] . . . is damaged by the highest peak energy in the reflective beam, producing a burn through spot diameter roughly ½ of the output beam diameter . . . ". And use of the complicated cooling channels in the capsule has not yet proven to be commercially viable.

A limited solution to the Fresnel reflection problem has been found by Peng et al. as described in U.S. Patent Publication No. 2009/0048585 and referred to herein as Peng '585. This work employs a method for cooling the fiber tip that is substantially less complex than that described in Griffiin '817. Peng '585 uses a thin walled transparent capsule of very limited diameter that fits loosely inside of an outer metal tube (see Prior Art FIG. 1F, below). This tube has hole in it that serves as a port for the side-fired laser beam. In operation, cooling fluid, typically water or saline solution, is made to flow in the gap between the outer surface of the transparent capsule and the inner surface of metal tube and this cooling fluid exits through the same port in the metal tube as the optical beam.

This fiber tip design has functioned satisfactorily when used in conjunction with a commercially available laser, a frequency doubled Nd:YAG laser, sold by Boston Scientific. Inc. that has been named the GreenLight laser due to its green, 0.532 micron wavelength, output. However, this tip design appears to be limited to use with lasers having output wavelengths, like the GreenLight laser, that exhibit very low optical attenuation in the aqueous cooling fluid and in the organic optical bonding agent used to secure the transparent capsule to the fiber. Hence, the Peng '585 fibers are sometimes referred to as the "GreenLight fibers" which emphasizes their limited spectral use.

Griffin '817 has pointed out that it became apparent when GreenLight fibers were used with the infrared Ho: YAG laser beam (having a 2.1 micron wavelength) that the organic optical bonding agent securing the cap to the fiber tip rapidly deteriorated under infrared illumination.

A second, and more serious problem with the GreenLight fibers described in Griffin '817 [Column 3 lines 30-35] is: The photo-thermal and/or photoacoustic shock waves that are generated by the [Ho: YAG] laser pulses and in the water are so intense that caps of similar dimensions to those used in the PVP [GreenLight] fiber can simply shatter to dust at average powers of 40 W or more. Thicker caps resist this damage but remain susceptible to erosion failures in apparent excess of that seen in PVP [GreenLight fiber].

To resolve the problem associated with the failed bonding agent as well as another problem related to the immobility of the fiber tip within the GreenLight fiber cap, Griffin '817 came up with a new design using a double cap arrangement. A very thin inner cap is fused directly onto the bare fiber end. Then, this sub-assembly is inserted into a secondary cap. (see Prior Art FIG. 1D, below). Significantly, the inner cap, containing the fiber, can be moved by the surgeon relative to the second (outer) cap so that if outer surface of the secondary cap were to become contaminated by surgical debris that could limit the power of the laser beam, it would be possible to simply move the fiber (and thereby the laser beam) to pass through a clear (unrestricted) area in the secondary capsule. While this appears to be a reasonable approach, in principle, the complexity associated with this tip design and the lack of direct cooling of the optical fiber (there remains a gap between the optical fiber and the inside wall of the inner cap) continue to raise serious concern.

Clearly, it would be a desirable objective to (1) simplify the design of side-fire fiber tips, (2) make them suitable for use with a broad range of surgical lasers with output wavelengths in both the visible and infrared portions of the optical spectrum, (3) make them more rugged by eliminating the need for organic bonding agents, and (4) extend their working life-time so that mid-procedure replacement would no longer be required during surgery.

SUMMARY OF THE INVENTION

This invention relates to a substantially different structure for the optical fiber tips than those discussed above that will ensure total internal reflection, essential for high power side-fire optical fiber tips, without the need for a relatively large hollow cavity adjacent to the beveled fiber surface on the fiber's tip nor the need for organic bonding agents. The objective behind changing the design and fabrication methods for the side-fire optical fiber tips is to achieve such a high level of function and durability that such tips will no longer fall into the category of disposables, to be used for only a single surgical procedure.

The new design recognizes that the Prior Art designs that employ transparent capsules with thin walls and substantial hollow empty spaces over the beveled fiber tips, as described in Griffin '817, will always tend to be frail and problematic both in product assembly and during surgical use.

In contrast, the new side-fire optical fiber tip is almost entirely solid to reduce geometrical thermal and mechanical stresses, which, in turn, produces a very robust structure. The solution of this problem came with the realization that the empty space behind the beveled tip of the fiber need be only several optical wavelengths thick to adequately assure the function of total internal reflection. The much larger volumes that are used in the present state-of-the-art fiber tip designs are not necessary but simply a matter of convenience to simplify assembly.

These thoughts led to a circularly-symmetric structure having a laser beam delivery fiber with a beveled end in line with a short stub fiber also with a beveled end. The gap between the two facing beveled fiber ends can be made to be in the range of, say, 50 microns or less, thinner than a half sheet of paper. When a thin walled fused silica cylindrical capillary tube is closely fit over the delivery fiber tip and the stub fiber tip and then fused (glass-to-glass) in place, the resulting structure is entirely solid except for the narrow gap between the fiber tips. No organic bonding agent is required. This robust structure will be more completely describe in the following two sections relating to the drawings.

BRIEF DESCRIPTION OF THE DRAWINGS

The above SUMMARY OF THE INVENTION as well as other features and advantages of the present invention over the Prior Art will be more fully appreciated by reference to the following detailed descriptions of illustrative embodiments in accordance with the present invention when taken in conjunction with the accompanying drawings, wherein:

FIG. 1E is another cross-sectional drawing of the Prior Art fiber tip design developed by Griffin '817.

FIG. 1F is a cross-sectional drawing of the Prior Art fiber tip design developed by Peng '585.

DETAILED DESCRIPTION OF THE DRAWINGS

Figure 1A:
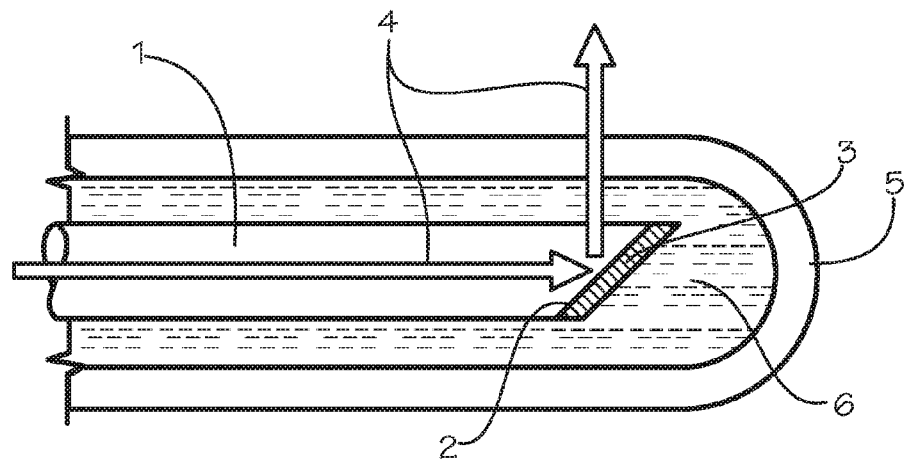
FIG. 1A is a cross-sectional drawing of the Prior Art fiber tip design developed by Brown '884.

FIG. 1A is a cross-sectional drawing of the Prior Art fiber tip design developed by Brown '884. An optical fiber, 1, has a beveled end 2 that is coated with a highly reflective coating 3. A laser beam 4 propagating down the axis of this fiber will reflect off of the beveled end 2 and be re-directed out though the side of the fiber. A loose fitting transparent capsule 5 containing a transparent fluid 6 is placed over the distal end of the beveled fiber for protection and possibly cooling. The tissue ablation zone (for example, in the case of BPH treatment) is immediately outside of the outer wall of this capsule 5. The fiber tip can be rotated or translated within the loose fitting transparent capsule either manually or automatically so that if the region on the capsule's outer surface where the laser beam passes become damaged or obscured by adherent surgical debris, a common occurrence, the surgical procedure can continue simply by moving the laser beam 89 to another position on the capsule's surface that is not damaged. This offers a significant advantage so that the surgical procedure may continue to a successful conclusion without a delay that would be required to replace or repair the fiber tip.

Unfortunately, in the years since Brown '884 was filed in 1993, no one has succeeded in developing a reflective coating 3 for an optical fiber that could endure a high power laser beam required for surgical applications for a sufficient period to complete a high power laser beam procedure, such as tissue ablation during BPH surgery. This represents a serious problem for the direct use of the Brown '884 design for side-fired fibers.

Figure 1B:
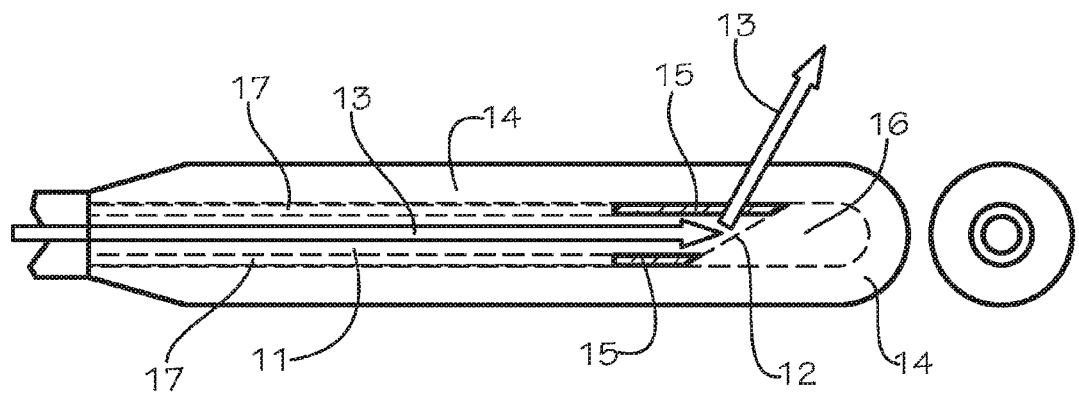
FIG. 1B is a cross-sectional drawing of the Prior Art fiber tip design developed by Pon '699.

FIG. 1B is a cross-sectional drawing of the Prior Art fiber tip design developed by Pon '699. In this case the optical fiber 11 also has a beveled end surface 12 but it has no reflective coating. Rather the laser beam 13 is reflected from the fiber end by the well-known process of total internal reflection. This is the same well known process that is used to guide light in all optical fibers. A gas or vacuum filled space 16 adjacent to the beveled end surface 12 of the optical fiber is established by the use of a transparent capsule 14 that is slid over the fiber tip and secured in place with an optically transparent bonding agent 15 that resists ingress of cooling and irrigation fluid and therefore leaving an empty hollow space above the beveled fiber surface 16 that is necessary for the total internal reflection process to occur. However, it was quickly learned that existing organic optical bonding agents exhibited marginal ability to survive under direct illumination of a high power surgical laser beam. One way used to resolve this problem was to move the bonding agent 15 between the fiber 11 and the transparent capsule 14 away from direct illumination of the side-fired laser beam further down the fiber from its tip to region 17.

Figure 1C:
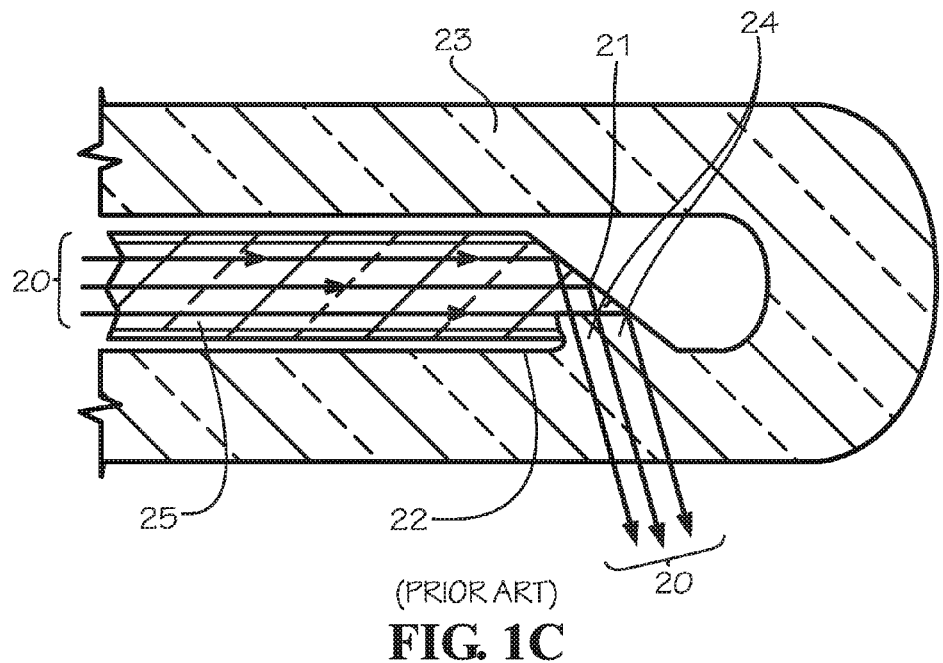
FIG. 1C is a cross-sectional drawing of the Prior Art fiber tip design developed by Brekke '499.

FIG. 1C is a cross-sectional drawing of the Prior Art fiber tip design developed by Brekke '499. The objective of this design is to fuse the tip 21 of the optical fiber 25 directly to the inner wall 22 of the capsule 23 to avoid unwanted Fresnel reflections. Unfortunately, Giffin '817 has reported that the fusion joint 24 between the fiber tip 21 and capsule 23 is susceptible to stress failure induced by a high power laser beam 20, shown as three parallel rays with arrows that indicate to direction of propagation of this laser beam 20.

Figure 1D:
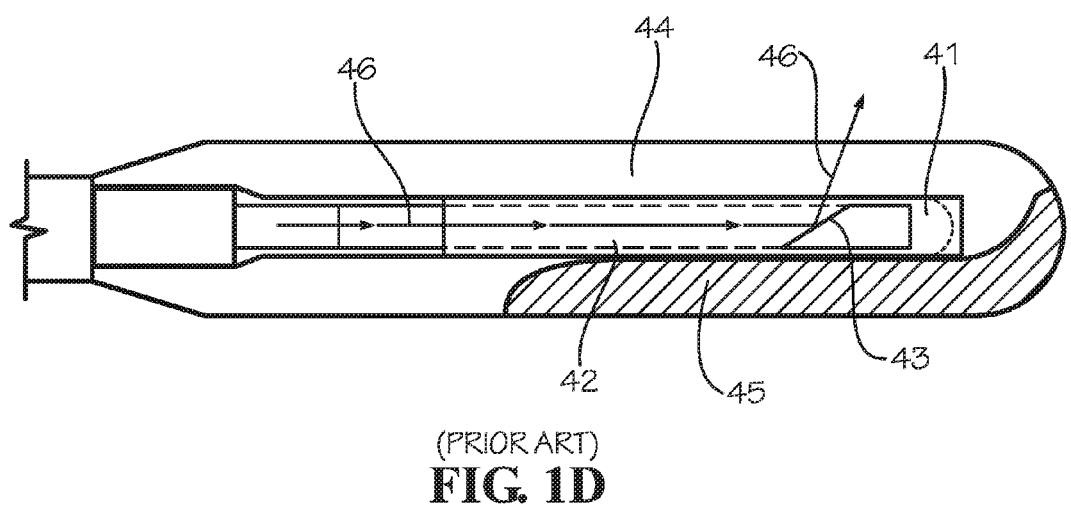
FIG. 1D is a cross-sectional drawing of the Prior Art fiber tip design developed by Griffin '817.

FIG. 1D is a cross-sectional drawing of the Prior Art fiber tip design developed by Giffin '817. A first capsule 41 containing an optical fiber 42 with a beveled end 43 is inserted into a second capsule 44. The shaded region 45 located on the outside surface of the second capsule 44 represents a mirror made by depositing a reflective gold coating. The purpose of this coating is to re-reflect any rays from the laser beam 46 that may have been reflected in the backward direction, due to Fresnel reflection, after passing through the fiber's side-wall and the inner surface of the first capsule.

FIG. 1E is another cross-sectional drawing of the Prior Art fiber tip design developed by Griffin '817. The fiber 51 and first (inner) capsule 52 are identical to the same parts shown in FIG. 1D. However, the second (outer) capsule 53 has a series of helical cooling channels 54 machined into the capsule's wall using a micro machining method, possibly employing a $CO_2$ laser beam.

FIG. 1F is a cross-sectional drawing of the Prior Art fiber tip design developed by Peng '585. In this design, the optical fiber 61 with a beveled tip 62 is contained inside of a transparent capsule 63 which is, in turn, located inside of a loose fitting meal tube 64. The metal tube 64 has a hole 65 to provide an exit port for the side-fired laser beam 66. In operation, cooling water or saline solution is forced down the annular gap between the outer surface of the transparent capsule 63 and the inner surface of the metal tube 64. This coolant eventually is exhausted through the same hole 65 in the metal tube that passes the laser beam. It is apparent that the fiber 61 cannot be translated or rotated within the metal tube 64 because the laser beam would then miss the hole 65 and strike the inner wall of the metal tube 64.

Figure 2:
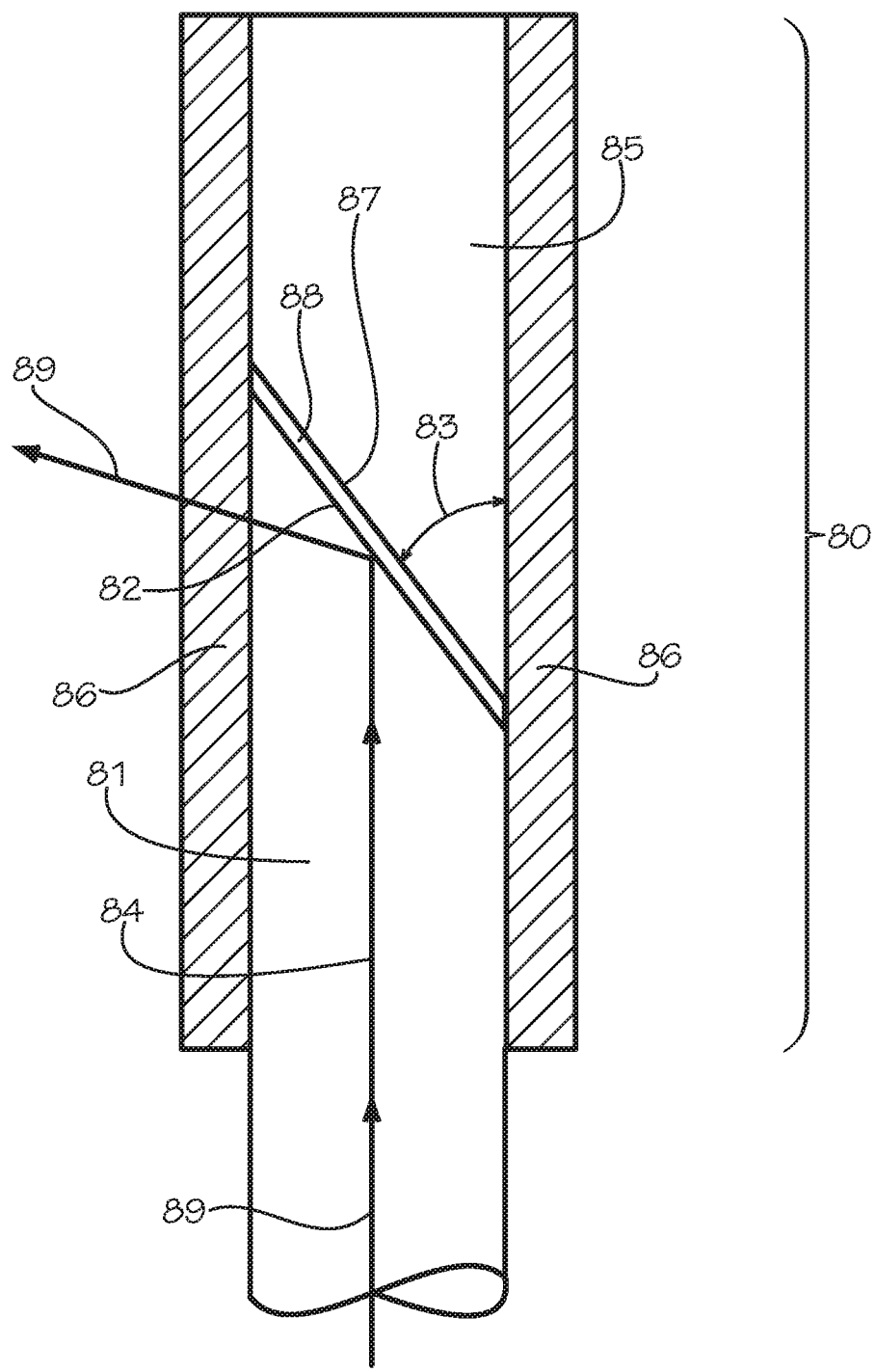
FIG. 2 is a cross-sectional drawing of the new fiber tip design introduced in this specification.

FIG. 2 is a cross-sectional drawing of the novel fiber tip assembly 80 that is the subject of this disclosure. A rugged side-fire fiber optical tip is made by joining together the following three components: (1) a laser beam delivery fiber 81 with a tip 82 that is beveled at an angle 83 of 39.5 degrees or less relative to the fiber's axis in order to support total internal reflection of a laser beam 84 transmitted in this fiber, (2) a short stub fiber 85 having the same outside diameter as the delivery fiber 81 and that is beveled 87 at one end with the same angle as the delivery fiber, and (3) a short transparent tube 86 having an inside diameter slightly larger than the outside diameters of the two fibers 81 and 85, that are assembled together by inserting the beveled ends of the delivery fiber 81 and stub fiber 85 fully into the transparent tube 86 so that the two beveled surfaces are parallel and separated by a narrow gap 88 followed by fusing these three components in place such that the small space associated with the gap between the two beveled fiber surfaces is hermetically sealed from the outside environment. This assembly results in a rugged structure that is completely inorganic and solid except for the space associated with the small gap 88 between the delivery fiber 81 and the stub fiber 85. The actual size of this gap must be greater than approximately 5 microns to support total internal reflection of the laser beam 89 and less than, say, 1,000 microns (1 mm) to ensure a rugged structure. The preferred size range for this gap would be in the range of 10 microns, to simplify positioning the fibers during set-up, and 100 microns to mitigate any stresses that would negatively impact durability and ruggedness of the tip structure.

Essentially all optical fibers used for laser surgery have pure fused silica cores that are surrounded by lower refractive index claddings made from fused silica that includes either a fluorine or boron oxide addition of no greater that 5 weight percent (to reduce the refractive index of the cladding). So, both the core and cladding regions have a high silica content (95% or greater) and their thermal expansion properties are quite well matched. In order to reduce thermally induced stresses during the fusion assembly of the tip structure, it is advantageous to select a capillary tube material that is also composed of 95 weight percent $SiO_2$, or greater. To achieve the most favorable final stresses in the tip structure, the capillary tube should be made either from pure fused silica (prepared by reacting silicon tetrachloride, $SiCl_4$, with oxygen, $O_2$) or fused quartz (naturally occurring crystalline $SiO_2$ that is melted into a glassy state). Specifically, if the $SiO_2$ concentration in the capillary tube is greater than that in the cladding region of the optical fibers, a favorable compressive stress is known to develop in the outer surface of the capillary tube upon cooling after fusion that will tend to strengthen the capillary tube. Here, it should be pointed out that glass (including fused silica) never fails under compressive stress. Rather, such a compressive stress must be overcome by a larger tensile stress before failure even becomes possible.

The details associated with the fusion step to produce the tip structure shown in FIG. 2 are important to achieve the desired hermetic seals between the delivery fiber and stub fiber and the capillary tube. Without such hermetic seals on both fibers, cooling fluid and/or irrigation fluid used during surgery could migrate into the gap 88 and frustrate the total internal reflection process that is relied upon to achieve the desired side-fire performance of the fiber tip. And due to the high silica content of both fibers and the capillary tube, high temperatures are required to achieve fusion. In fact, the temperatures are so high that there are only several options for the fusion heating source. They are (1) an oxyhydrogen flame, (2) an electric arc, or (3) a $CO_2$ laser beam (or some other laser having a beam wavelength that is strongly absorbed by $SiO_2$). Prior to the actual fusion step, the delivery fiber and stub fiber must be carefully set into position. During this setup, it is necessary that the inside diameter of the capillary tube is larger than the outside diameter of the fibers so that it is possible to insert the fibers into the capillary tube with very little or no friction. Yet, the difference in these diameters should be small enough so that it is unlikely to entrap gas between the fiber and capillary tube during the subsequent fusion step. A difference in the inside diameter of the capillary and the outside diameter of the two fibers of 100 microns or less is preferred.

Based on the limited clearance between the fibers and the capillary tube and the generally small sizes of these parts, it is apparent that it would be helpful to employ optical magnification and micro-manipulators to assist in the insertion of the fibers into the capillary tube and to verify that the gap 88 is properly set before the fusion step is initiated. It is also helpful if the stub fiber's length prior to fusion is extended several inches so that this fiber can be easily handled by gripping the extension during insertion without inadvertently disturbing the position of the capillary tube. Then, after fusion is completed, the stub fiber's extension can be cut back to its desired final length.

It is advantageous to accomplish the final fusion step using fixtures to hold the delivery fiber and stub fiber into alignment along a common horizontal axis. These fixtures should contact the fibers sufficiently far away from the capillary tube so that they will not overheat during the fusion step. Experience has shown that during fusion, it is preferred to use a small localized heating source, smaller than the length of the capillary tube so that the tip assembly does not tend to sag when it reaches fusion temperature. To mitigate any tendency to sag, the entire fiber tip assembly may be slowly rotated on its axis (as can be done using a small glass working lathe) during the fusion step. However, this rotation is not essential if the hot fusion zone is kept small.

Experience has shown that when a fused silica tube (e.g., the capillary tube) is heated to a sufficiently high temperature it will become soft and circumferential surface tension will cause the tube to decrease in diameter while the wall thickness increases. If there is a solid cylinder of fused silica (e.g., an optical fiber) loosely fit inside of the soft heated tube, the tube's outside diameter will eventually shrink down and make broad contact with the surface of the cylinder and a fusion joint will form. During such a fusion step, it is preferable to first apply the fusion heat to the surface of either the delivery fiber or the stub fiber several millimeters away from the capillary tube. Then the heat zone should be progressively moved towards the capillary tube, then over the surface of the capillary tube, and finally for several more millimeters along the opposite fiber. This method for heating is advantageous to ensure that any gas remaining between the surfaces of the fibers and the inside surface of the capillary tube will have an exit path ahead of the hot fusion zone and thereby eliminate any bubbles or un-bonded regions in the fusion joint. Use of a helium gas atmosphere, rather than air, in the vicinity of the fusion zone is helpful because helium will be absorbed within the structure of the hot fused silica parts without a tendency to form bubbles or any other negative effects. In some cases, more than a single fusion pass may be necessary to ensure that the capillary tube has completely collapsed onto the surfaces of the fibers and that the tube and fibers are fully bonded forming hermetic seals at both ends of the tube. After the bonding operation, the quality of the seal can be checked with a helium leak detection test by immersing the tip assembly into a helium atmosphere for several minutes—then removing the tip for, say, 30 minutes—then inserting the tip into a helium mass spectrometer used for helium leak detection. If the seal between the fibers and the capillary were not hermetic, some helium gas would enter the gap region during the immersion in the helium atmosphere and it would continue to leak out and be detected during the subsequent leak detection test.

In order for this fiber optic tip assembly 80 to fit into the limited channel diameters available in surgical cystoscopes or endoscopes (typically, 2 to 3 mm in diameter) and still have space for the flow of cooling/irrigation fluid, it is desirable to keep the outer diameter of the fused capillary region relatively small. This, in turn, implies a relatively thin wall thickness for the capillary tube. The preferred range would be, say, 100 microns or greater to give the capillary tube sufficient strength for handling during tip assembly and less than 300 microns so that the outside diameter of the entire tip assembly including a typical 600 micron diameter optical fiber is less than, say, 1,200 microns (1.2 mm).

Figure 3:
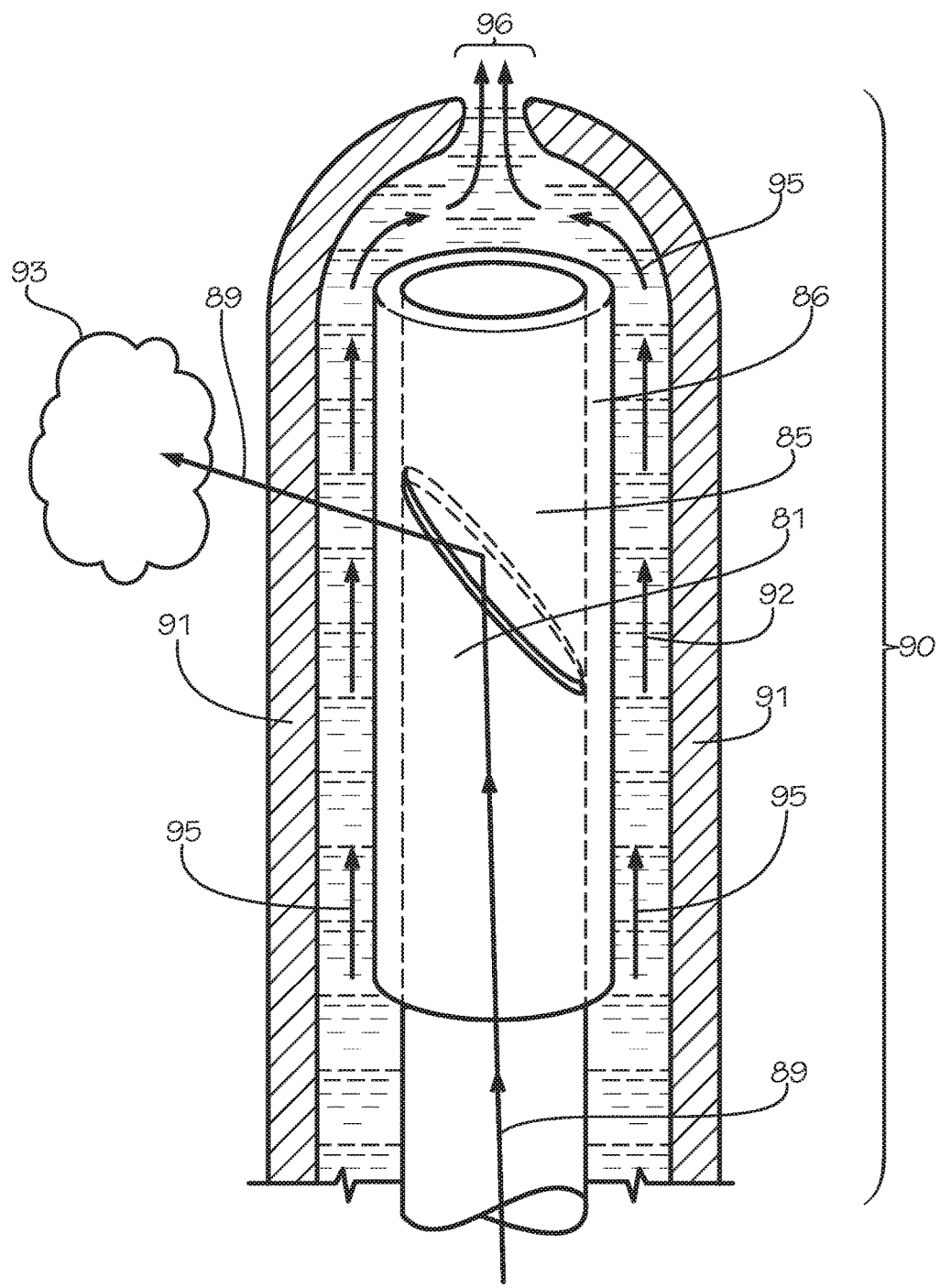
FIG. 3 is a perspective drawing of the fiber tip assembly shown in FIG. 2 that is inserted into a transparent capsule (shown in cross-section)

FIG. 3 is a perspective drawing of the fiber optic tip assembly 80 shown in FIG. 2 that is inserted into a transparent capsule 91 (shown in cross-section) containing a cooling/irrigating fluid 92 to form a complete fiber optic tip device 90. The purpose of this capsule 91 is to provide a mechanical and optical barrier between the fiber tip assembly and the surgical site (target) 93. The side-fire laser beam 94 must pass through the cylindrical wall of the capsule 91 to impinge on the surgical site 93. Typical dimensions for capsule would be approximately 2,000 microns (2 mm) in outside diameter, 200 micron wall thickness, and 8 to 10 mm long. This would allow for a circularly symmetric gap between the inner surface of the capsule and the outer surface of the fiber tip assembly (assuming a 1,200 micron outer diameter for the fiber optic tip device 90) of approximately 200 microns, through which cooling/irrigation fluid could flow in the direction of the arrows 95. The cooling/irrigation flow could pass out of an optional opening in the distal end 96 of the capsule 91. For some surgical laser wavelengths in the visible and near infrared, shorter than 1.1 microns, normal water or saline solution is sufficiently transparent to be used as an irrigation fluid. For longer infrared wavelengths, including 1.47 microns, the use of heavy water or a heavy water based saline solution is preferred due to its greater transparency. (See Cross Reference cited in § 1, above, U.S. Provisional Patent Application Ser. No. 62/252,471 titled LASER SURGERY EMPLOYING HEAVY WATER TO ENHANCE LASER BEAM TRANSMISSION.) In some applications, it may be helpful to limit the use of heavy water only to surround the fiber tip located inside of a closed-ended capsule 91. In these applications, that do not include the flow of heavy water for irrigation, only a very limited amount of heavy water is required to fill the capsule to serve as a highly transparent medium to transmit the laser beam and to provide a degree of refractive index matching to reduce reflections of the laser beam within the capsule.

It is significant to recognize that the tissue ablation zone (for example, in the case of BPH treatment) is immediately outside of the outer wall of the capsule 91. And during ablation, the outer surface of this capillary may come in direct contact with ablated tissue debris that can stick to this surface and become further heated by the high power laser beam. The heating may become so intense that it can cause the tissue to deposit an adherent opaque layer onto the outer surface of the capillary tube due to carbonization (burning off of the oxygen and hydrogen content in the tissue and leaving a darkish carbon residue). This darkish residue will selectively absorb more of the energy in the laser beam 94 so that if the surgical procedure is continued without modification, localized heating of the capillary wall will ultimately overwhelm the cooling capacity of the internal cooling fluid and the wall will likely deteriorate and, possibly, fail leading to fractured glass and spilled cooing fluid—a very undesirable situation.

The solution to this problem is to provide a feedback mechanism, either to the surgeon or automatically to a controller, so that the surgical procedure may be either modified or terminated to avoid such a catastrophic failure. The preferred remedial procedure would be to either translate or rotate the fiber tip assembly within the capillary tube 91 so that if the capillary tube's wall becomes obstructed in a specific area by surgical debris, the tip assembly can be repositioned to another location where the wall is clear of such debris. This offers a significant advantage so that the surgical procedure may continue to a successful conclusion without the need to replace the fiber tip. This strategy eliminates the concern of surgeons that their fiber tip assembly might become opaque due to build-up of carbonized tissue debris and require replacement before an operating procedure is finished.

While motion of the fiber tip assembly relative to the capsule by a surgeon, as needed, to present a clear region of the capsule's wall to the laser beam 94 is a viable, it is also possible to automate the relative motion so that the surgeon does not even need to be concerned with the carbonization of tissue debris on the capsule's outer surface. The strategy would be to automatically move the capsule in a slow helical pattern relative to the fiber tip assembly using a motor drive so that that over the course of a BPH treatment that lasts between 15 and 45 minutes (depending on the mass of tissue ablated) every minute or so the laser beam would pass through to a "fresh" (clean) surface area of the capillary. So, if during the operation, the surgeon noticed that the optical power level reaching the tissue targeted for removal has been diminished by debris, he need only wait a minute or less for a "fresh" clear area of the capillary tube to be exposed to the laser beam before continuing with the operation.

Based on a simple analysis, one can confirm that the laser beam diameter transmitted by a typical 600 micron core diameter fiber with a numerical aperture of 0.22 would diverge to a diameter of 1 mm at the location where it exited from the exterior surface of a 2 mm diameter capsule. If the length of this capsule were 8 mm, it would have a total outside cylindrical surface area of 50 square mm (2 mm×π×8 mm=50 square mm). And if every minute, or so, slow helical rotation of the cylinder presented a fresh 1 mm square area to the laser beam, this rotation could continue for 50 minutes—longer than the maximum time of 45 minutes reported for BPH treatments.

A significant consequence of employing such an automated procedure is that fiber tip assembly would be preserved for use during subsequent procedures and only the inexpensive capsule that could be secured to a cannula would be disposable. In fact, a damaged used capsule could be quickly removed and replaced without removing the surgical fiber from the cannula.

While the above disclosure describes a fiber optical side-fire tip design and assembly method that can be beneficially used in some exemplary laser surgery procedures, these examples should merely be considered to be representative of many others. It is therefore to be understood that the scope of this invention is broader than the methods and procedures described in the specification and following claims and that the apparatus and methods described herein relate broadly to the design, assembly and use of the described side-fire fiber optic tip.

The invention claimed is:

1. A side-fire fiber optical tip fabricated by joining together the following three components: (1) a laser beam delivery fiber with a tip that is beveled at an angle to the fiber's axis to support total internal reflection of a laser beam transmitted in the fiber, (2) a short stub fiber of the same outside diameter as the delivery fiber and that is beveled at one end with the same angle as the delivery fiber, and (3) a short transparent tube having an inside diameter slightly larger than the outside diameters of the two fibers, that are assembled together by inserting the beveled ends of the delivery fiber and stub fiber fully into the transparent tube so that the two beveled surfaces are parallel and separated by a narrow gap followed by fusing these three components in place such that the small space associated with the gap between the two beveled fiber surfaces is designed to be hermetically sealed and a helium leak detection test is employed to determine if the small sealed space associated with the gap between the said two beveled fiber end surfaces is hermetic.

2. The side-fire fiber optical tip as described in claim 1 in which all three said components are made from fused silica or fused quartz containing at least 95% silicon dioxide ($SiO_2$).

3. The side-fire fiber optical tip a described in claim 2 in which the $SiO_2$ concentration in the transparent tube is equal or exceeds the $SiO_2$ concentration in the outer surfaces of the delivery fiber and the stub fiber.

4. The side-fire fiber optical tip as described in claim 1 in which the beveled angle between the beveled surface and the fiber's axis is 39.5 degrees or less.

5. The side-fire fiber optical tip as described in claim 1 in which the narrow gap as measured in the axial direction between the two beveled surfaces on the fibers is between 5 microns and 1 mm.

6. The side-fire fiber optical tip as described in claim 1 in which the narrow gap as measured in the axial direction between the two beveled surfaces on the fibers is between 10 microns and 100 microns.

7. The side-fire fiber optical tip as described in claim 1 in which the inside diameter of the said transparent tube before fusing is less than 100 microns larger than the diameter of the optical fibers that are inserted into this tube.

8. A method for fabricating the side-fire fiber optical tip as described in claim 1 using an electric arc as the heat source in a helium gas atmosphere about the fusion zone while fusing the optical fibers to the transparent tube.

9. A method for fabricating the side-fire fiber optical tip as described in claim 1 using a $CO_2$ laser beam as the heat source in a helium gas atmosphere about the fusion zone while fusing the optical fibers to the transparent tube.

10. A method for fabrication the side-fire optical fiber tip as described in claim 1 by progressively advancing a localized hot spot produced by any fusing source starting several millimeters before the junction where the delivery fiber enters the transparent tube to several millimeters beyond the junction where the stub fiber exits the transparent tube.

11. A method for fabricating the side-fire optical fiber tip as described in claim 1 by progressively advancing a localized hot spot produced by any fusing source starting several millimeters before the junction where the stub fiber enters the transparent tube to several millimeters beyond the junction where the delivery fiber exits the transparent tube.

12. A side-fire fiber optical tip as described in claim 1 which is located inside of a loosely fitting transparent capsule that contains a transparent liquid.

13. A side-fire fiber optical tip as described in claim 12 in which the distal end of the said capsule is sealed.

14. A side-fire fiber optical tip as described in claim 12 in which the distal end of the said capsule has an opening through which the transparent liquid can flow.

15. A side-fire fiber optical tip as described in claim 13 or claim 14 in which the transparent liquid is normal water or saline solution.

16. A side-fire fiber optical tip as described in claim 13 or claim 14 in which the transparent liquid is heavy water or heavy water/saline solution.

17. A side-fire fiber optical tip contained in a capsule as described in claim 12 in which the capsule may be rotated and translated relative to the fiber tip assembly either manually or automatically.

18. A side-fire fiber optical tip contained in a capsule as described in claim 17 in which the capsule is secured to a cannula with a leak tight joint that can be easily opened and closed to replace the capsule while the delivery optical fiber remains in place inside of the cannula.

19. A side-fire fiber optical tip as in claim 12 that loosely fits inside of a transparent capsule such that the fiber can rotated and/or translated either manually or automatically relative to the capsule and that the capsule is secured to a cannula containing a liquid that can flow along the outer surface of the delivery fiber before passing out of an opening in the distal tip of the capsule.

* * * * *